(12) United States Patent
Ansmann et al.

(10) Patent No.: US 6,562,876 B1
(45) Date of Patent: May 13, 2003

(54) USE OF AQUEOUS WAX DISPERSIONS AS CONSISTENCY PROVIDERS

(75) Inventors: Achim Ansmann, Erkrath (DE); Nicole Mertscheit, Hilden (DE); Rolf Kawa, Monheim (DE)

(73) Assignee: Cognis Deutschland GmbH & Co. KG, Duesseldorf (DE)

(*) Notice: Subject to any disclaimer, the term of this patent is extended or adjusted under 35 U.S.C. 154(b) by 0 days.

(21) Appl. No.: 09/763,220

(22) PCT Filed: Aug. 11, 1999

(86) PCT No.: PCT/EP99/05906

§ 371 (c)(1),
(2), (4) Date: Apr. 23, 2001

(87) PCT Pub. No.: WO00/10510

PCT Pub. Date: Mar. 2, 2000

(30) Foreign Application Priority Data

Aug. 20, 1998 (DE) .................................. 198 37 841

(51) Int. Cl.⁷ .............................. A61K 7/00; B01F 3/08; B01F 17/56; C08L 91/06

(52) U.S. Cl. ...................... 516/77; 106/271; 514/943; 516/925

(58) Field of Search ............. 516/77, 925; 106/271; 510/416, 417; 514/943

(56) References Cited

U.S. PATENT DOCUMENTS

| | | | | |
|---|---|---|---|---|
| 3,971,733 A | * | 7/1976 | Hawkins .................. 516/77 X |
| 4,172,887 A | | 10/1979 | Vanlerberghe et al. ........ 424/70 |
| 4,269,739 A | * | 5/1981 | Grejsner .................. 510/417 X |
| 4,388,138 A | * | 6/1983 | Brown et al. ............ 106/271 X |
| 4,434,008 A | * | 2/1984 | Dumm et al. ................ 106/271 |
| 4,777,038 A | | 10/1988 | Scheuffgen ................ 424/70 |
| 4,824,594 A | | 4/1989 | Hoeffkes et al. |
| 5,296,166 A | * | 3/1994 | Leong ...................... 516/77 |
| 5,389,282 A | * | 2/1995 | Saijo et al. |
| 5,431,840 A | * | 7/1995 | Soldanski et al. ...... 510/417 X |
| 5,560,873 A | | 10/1996 | Chen et al. ............... 510/123 |
| 5,646,106 A | | 7/1997 | Chen et al. ............... 510/416 |
| 5,705,169 A | | 1/1998 | Stein et al. ................ 424/401 |
| 5,730,960 A | | 3/1998 | Stein et al. ................ 424/59 |
| 6,193,960 B1 | | 2/2001 | Metzger et al. ............. 424/59 |

FOREIGN PATENT DOCUMENTS

| | | |
|---|---|---|
| DE | 1 165 574 | 3/1964 |
| DE | 20 24 051 | 12/1971 |
| EP | 0 693 471 | 7/1995 |
| EP | 0 694 521 A1 | 1/1996 |
| EP | 0 818 450 A1 | 1/1998 |
| FR | 2 252 840 | 6/1975 |
| GB | 962919 | 7/1964 |
| GB | 1 333 475 | 10/1973 |
| WO | WO 97/13498 | 4/1997 |

OTHER PUBLICATIONS

Todd, et al., "Volatile Silicone Fluids For Cosmetic Formulations," Cosm. Toil. 91, 27, pp 29–32 (1976).

Tronnier, et al., "Experimentelle Untersuchungen zur Wirkungsweise aluminiumhaltiger Antiperspiranzien," J. Soc. Cosmetic Chemists 24, 281–290 (1973).

Graham, et al. "Inhibition of the mitochondrial oxidation of octanoate by salicylic acid and related compounds," J. Pharm. Pharmcol. 26, 531 (1974).

Lochhead, et al., "Encyclopedia of Polymers and Thickeners for Cosmetics," Cosm. Toil 108, pp. 95–135, (1993).

P. Finkel, "Formulierung kosmetischer Sonnenschutzmittel," SÖFW–Journal, 122, pp. 543–548 (1996).

"Kosmetische Färbemittel" of the Farbstoffkommission der Deutschen Forschungsgemeinschaft, Verlag Chemie, Weinheim, 1984, pp. 81–106.

* cited by examiner

*Primary Examiner*—Richard D. Lovering
(74) *Attorney, Agent, or Firm*—John E. Drach; Steven J. Trzaska

(57) ABSTRACT

A process for cold-producing an oil-in-water emulsion having enhanced consistency and tactile properties involving: (a) providing an oil component; (b) providing an aqueous wax dispersion containing: (i) a wax component; and (ii) an emulsifier; (c) providing water; and (d) cold-stirring (a)–(c) to form the emulsion.

8 Claims, No Drawings

USE OF AQUEOUS WAX DISPERSIONS AS CONSISTENCY PROVIDERS

This application is a 371 of PCT/EP99/05906 filed Aug. 11, 1999.

BACKGROUND OF THE INVENTION

This invention relates generally to cosmetic emulsions and more particularly to the use of special wax dispersions as consistency providers.

Today, fine-droplet cosmetically elegant emulsions are often produced by the PIT process. In this process, the constituents of the emulsion are first heated beyond the phase inversion temperature and then slowly cooled. It is obvious that this process is time- and energy-consuming and that it would be desirable to produce comparable emulsions by so-called cold techniques. Although it is of course possible in principle to stir the liquid constituents of an emulsion in the cold state, this has a number of disadvantages in relation to the PIT method. Thus, the emulsions are generally coarser and separate quickly, especially at elevated temperatures, and in particular have unattractive sensorial properties, i.e. feel insubstantial. If known consistency providers, for example fatty alcohols or partial glycerides, are added to the "cold-produced" emulsions, they are unable to develop viscosities as high as those obtained, for example, by the PIT method and, in addition, destabilize the emulsions.

Accordingly, the problem addressed by the present invention was to find a way of obtaining o/w emulsions that would be distinguished by fine droplets, storage stability, heat resistance, sufficiently high viscosity and pleasant sensorial properties by the cold route.

DESCRIPTION OF THE INVENTION

The present invention relates to the use of aqueous dispersions containing
(a) waxes and
(b) emulsifiers
as consistency providers for the cold production of o/w emulsions.

Waxes

Suitable waxes are, for example, alkylene glycol esters; fatty acid alkanolamides; partial glycerides; esters of polybasic, optionally hydroxysubstituted carboxylic acids with fatty alcohols containing 6 to 22 carbon atoms; fatty compounds such as, for example, fatty alcohols, fatty ketones, fatty aldehydes, fatty ethers and fatty carbonates; ring-opening products of olefin epoxides containing 12 to 22 carbon atoms with fatty alcohols containing 12 to 22 carbon atoms and/or polyols containing 2 to 15 carbon atoms and 2 to 10 hydroxyl groups; and mixtures thereof.

Alkylene glycol esters. The alkylene glycol esters are normally monoesters and/or diesters of alkylene glycols corresponding to formula (I):

$$R^1CO(OA)_nOR^2 \quad (I)$$

in which $R^1CO$ is a linear or branched, saturated or unsaturated acyl group containing 6 to 22 carbon atoms, $R^2$ is hydrogen or has the same meaning as $R^1CO$ and A is a linear or branched alkylene group containing 2 to 4 carbon atoms and n is a number of 1 to 5. Typical examples are monoesters and/or diesters of ethylene glycol, propylene glycol, diethylene glycol, dipropylene glycol, triethylene glycol or tetraethylene glycol with fatty acids containing 6 to 22 and preferably 12 to 18 carbon atoms, such as caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof. Ethylene glycol monostearate and/or distearate is/are particularly preferred.

Fatty acid alkanolamides. Fatty acid alkanolamides which are suitable as waxes correspond to formula (II)

$$R^3CO-NR^4-B-OH \quad (I)$$

in which $R^3CO$ is a linear or branched, saturated or unsaturated acyl group containing 6 to 22 carbon atoms, $R^4$ is hydrogen or an optionally hydroxysubstituted alkyl group containing 1 to 4 carbon atoms and B is a linear or branched alkylene group containing 1 to 4 carbon atoms. Typical examples are condensation products of ethanolamine, methyl ethanolamine, diethanolamine, propanolamine, methyl propanolamine and dipropanolamine and mixtures thereof with caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof. Stearic acid ethanolamide is particularly preferred.

Partial glycerides. Partial glycerides which have wax properties are monoesters and/or diesters of glycerol with fatty acids, i.e. for example caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof. They correspond to formula (III):

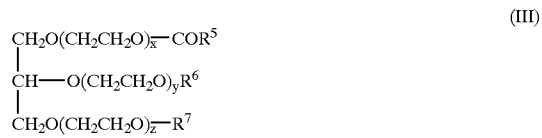

$$\begin{aligned} &CH_2O(CH_2CH_2O)_{\overline{x}}COR^5 \\ &CH-O(CH_2CH_2O)_yR^6 \\ &CH_2O(CH_2CH_2O)_{\overline{z}}R^7 \end{aligned} \quad (III)$$

in which $R^5CO$ is a linear or branched acyl group containing 6 to 22 carbon atoms, $R^6$ and $R^7$ independently of one another represent hydrogen or have the same meaning as $R^5CO$, x, y and z together stand for 0 or for a number of 1 to 30 and X is an alkali or alkaline earth metal, with the proviso that at least one of the two substituents $R^6$ and $R^7$ is hydrogen. Typical examples are lauric acid monoglyceride, lauric acid diglyceride, coconut oil fatty acid monoglyceride, coconut fatty acid triglyceride, palmitic acid monoglyceride, palmitic acid triglyceride, stearic acid monoglyceride, stearic acid diglyceride, isostearic acid monoglyceride, isostearic acid diglyceride, oleic acid monoglyceride, oleic acid diglyceride, tallow fatty acid monoglyceride, tallow fatty acid diglyceride, behenic acid monoglyceride, behenic acid diglyceride, erucic acid monoglyceride, erucic acid diglyceride and technical mixtures thereof which may still contain small quantities of triglyceride from the production process.

Polybasic carboxylic acid and hydroxycarboxylic acid esters. Other suitable waxes are esters of polybasic, optionally hydroxysubstituted carboxylic acids with fatty alcohols containing 6 to 22 carbon atoms. The acid component of these esters may be selected, for example, from malonic acid, maleic acid, fumaric acid, adipic acid, sebacic acid, azelaic acid, dodecanedioic acid, phthalic acid, isophthalic acid and, more particularly, succinic acid and also malic acid, citric acid and, more particularly, tartaric acid and mixtures thereof. The fatty alcohols contain 6 to 22, preferably 12 to 18 and more preferably 16 to 18 carbon atoms in the alkyl chain. Typical examples are caproic alcohol, caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and technical mixtures thereof. The esters may be present as full or partial esters; monoesters and, above all, diesters of carboxylic or hydroxycarboxylic acids preferably being used. Typical examples are succinic acid mono- and dilauryl ester, succinic acid mono- and dicetearyl ester, succinic acid mono- and distearyl ester, tartaric acid mono- and dilauryl ester, tartaric acid mono- and dicocoalkyl ester, tartaric acid mono- and dicetearyl ester, citric acid mono-, di- and trilauryl ester, citric acid mono-, di- and tricocoalkyl ester and citric acid mono-, di- and tricetearyl ester.

Fatty alcohols. Another group of waxes are long-chain fatty alcohols corresponding to formula (IV):

$$R^8OH \qquad (IV)$$

in which $R^8$ is a linear alkyl group containing 16 to 48 and preferably 18 to 22 carbon atoms. The substances mentioned are generally based on vegetable or animal fatty acids or are oxidation products of long-chain paraffins.

Fatty ketones. Fatty ketones suitable as component (a) preferably correspond to formula (V):

$$R^9-CO-R^{10} \qquad (V)$$

in which $R^9$ and $R^{10}$ independently of one another represent alkyl and/or alkenyl groups containing 1 to 22 carbon atoms, with the proviso that they contain a total of at least 24 and preferably 32 to 48 carbon atoms. The ketones may be prepared by known methods, for example by pyrolysis of the corresponding fatty acid magnesium salts. The ketones may be symmetrical or non-symmetrical, although the two substituents $R^9$ and $R^{10}$ preferably differ from one another by only one carbon atom and are derived from fatty acids containing 16 to 22 carbon atoms. Stearone is distinguished by particularly advantageous properties.

Fatty aldehydes. Fatty aldehydes suitable as waxes correspond to formula (VI):

$$R^{11}COH \qquad (VI)$$

in which $R^{11}CO$ is a linear or branched acyl group containing 16 to 48 and preferably 18 to 22 carbon atoms.

Fatty ethers. Other suitable waxes are fatty ethers corresponding to formula (VI):

$$R^{12}-O-R^{13} \qquad (VII)$$

in which $R^{12}$ and $R^{13}$ independently of one another represent alkyl and/or alkenyl groups containing 1 to 22 carbon atoms, with the proviso that they contain a total of at least 24 and preferably 32 to 48 carbon atoms. Fatty ethers of the type mentioned are normally prepared by acidic condensation of the corresponding fatty alcohols. Fatty ethers with particularly advantageous properties are obtained by condensation of fatty alcohols containing 16 to 22 carbon atoms such as, for example, cetyl alcohol, cetearyl alcohol, stearyl alcohol, isostearyl alcohol, oleyl alcohol, behenyl alcohol and/or erucyl alcohol.

Fatty carbonates. Component (a) may also be selected from fatty carbonates corresponding to formula (VIII):

$$R^{14}O-CO-OR^{15} \qquad (VIII)$$

in which $R^{14}$ and $R^{15}$ independently of one another are alkyl and/or alkenyl groups containing 1 to 22 carbon atoms, with the proviso that they contain a total of at least 24 and preferably 32 to 48 carbon atoms. The substances are obtained by transesterifying dimethyl or diethyl carbonate, for example, with the corresponding fatty alcohols by methods known per se. Accordingly, the fatty carbonates may be symmetrical or non-symmetrical. However, carbonates in which $R^{14}$ and $R^{15}$ are the same and represent alkyl groups containing 16 to 22 carbon atoms are preferably used. Transesterification products of dimethyl or diethyl carbonate with cetyl alcohol, cetearyl alcohol, stearyl alcohol, isostearyl alcohol, oleyl alcohol, behenyl alcohol and/or erucyl alcohol in the form of their monoesters and diesters and technical mixtures thereof are particularly preferred.

Fatty acids. Other suitable waxes are fatty acids corresponding to formula (IX):

$$R^{16}CO-OH \qquad (IX)$$

in which $R^{16}CO$ is a linear or branched, optionally hydroxy-functionalized acyl group containing 16 to 24 carbon atoms. Palmitic acid, stearic acid, hydroxystearic acid and in particular behenic acid are preferably used.

Epoxide ring-opening products. The ring-opening products are known substances which are normally obtained by acidcatalyzed reaction of terminal or internal olefin epoxides with aliphatic alcohols. The reaction products preferably correspond to formula (X):

(X)

in which $R^{17}$ and $R^{18}$ represent hydrogen or an alkyl group containing 10 to 20 carbon atoms, with the proviso that the sum total of carbon atoms of $R^{17}$ and $R^{18}$ is between 10 and 20 and $R^{19}$ is an alkyl and/or alkenyl group containing 12 to 22 carbon atoms and/or the residue of a polyol containing 2 to 15 carbon atoms and 2 to 10 hydroxyl groups. Typical examples are ring-opening products of α-dodecene epoxide, α-hexadecene epoxide, α-octadecene epoxide, α-eicosene epoxide, α-docosene epoxide, i-dodecene epoxide, i-hexadecene epoxide, i-octadecene epoxide, i-eicosene epoxide and/or i-docosene epoxide with lauryl alcohol, cocofatty alcohol, myristyl alcohol, cetyl alcohol, cetearyl alcohol, stearyl alcohol, isostearyl alcohol, oleyl alcohol, elaidyl alcohol, petroselinyl alcohol, linolyl alcohol, linolenyl alcohol, behenyl alcohol and/or erucyl alcohol. Ring opening products of hexa- and/or octadecene epoxides with fatty alcohols containing 16 to 18 carbon atoms are preferably used. If polyols are used instead of the fatty alcohols for the ring opening reaction, they are selected for example from the following substances: glycerol; alkylene glycols such as, for example, ethylene glycol, diethylene glycol, propylene glycol, butylene glycol, hexylene glycol and polyethylene glycols with an average molecular weight of 100 to 1,000 dalton; technical oligoglycerol mixtures with a degree of self-condensation of 1.5 to 10 such as, for example, technical diglycerol mixtures with a diglycerol content of 40 to 50% by weight; methylol compounds such as, in particular, trimethylol ethane, trimethylol propane, trimethylol butane, pentaerythritol and dipentaerythritol; lower alkyl glucosides, more particularly those containing 1 to 8 carbon atoms in the alkyl chain such as, for example, methyl and butyl glucoside; sugar alcohols containing 5 to 12 carbon atoms such as, for example, sorbitol or mannitol, sugars containing 5 to 12 carbon atoms such as, for example, glucose or sucrose; amino sugars such as, for example, glucamine.

Emulsifiers

Suitable emulsifiers are, for example, nonionic surfactants from at least one of the following groups:

(1) products of the addition of 2 to 30 moles of ethylene oxide and/or 0 to 5 moles of propylene oxide onto linear fatty alcohols containing 8 to 22 carbon atoms, onto fatty acids containing 12 to 22 carbon atoms and onto alkylphenols containing 8 to 15 carbon atoms in the alkyl group;

(2) $C_{12/18}$ fatty acid monoesters and diesters of products of the addition of 1 to 30 moles of ethylene oxide onto glycerol;

(3) glycerol monoesters and diesters and sorbitan monoesters and diesters of saturated and unsaturated fatty acids containing 6 to 22 carbon atoms and ethylene oxide adducts thereof;

(4) alkyl mono- and oligoglycosides containing 8 to 22 carbon atoms in the alkyl group and ethoxylated analogs thereof;

(5) adducts of 15 to 60 moles of ethylene oxide with castor oil and/or hydrogenated castor oil;

(6) polyol esters and, in particular, polyglycerol esters such as, for example, polyglycerol polyricinoleate, polyglycerol poly-12-hydroxy-stearate and polyglycerol dimerate. Mixtures of compounds from several of these classes are also suitable;

(7) products of the addition of 2 to 15 moles of ethylene oxide onto castor oil and/or hydrogenated castor oil;

(8) partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);

(9) mono-, di- and trialkyl phosphates and mono-, di- and/or tri-PEG-alkyl phosphates and salts thereof;

(10) wool wax alcohols;

(11) polysiloxane/polyalkyl polyether copolymers and corresponding derivatives;

(12) mixed esters of pentaerythritol, fatty acids, citric acid and fatty alcohol according to DE-PS 1165574 and/or mixed esters of fatty acids containing 6 to 22 carbon atoms, methyl glucose and polyols, preferably glycerol or polyglycerol, and

(13) polyalkylene glycols.

The addition products of ethylene oxide and/or propylene oxide with fatty alcohols, fatty acids, alkylphenols, glycerol monoesters and diesters and sorbitan monoesters and diesters of fatty acids or with castor oil are known, commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide with glycerol are known as refatting agents for cosmetic formulations from DE-PS 20 24 051.

$C_{8/18}$ alkyl mono- and oligoglycosides, their production and their use as surfactants are known from the prior art. They are produced in particular by reacting glucose or oligosaccharides with primary $C_{8/18}$ alcohols. So far as the glycoside unit is concerned, both monoglycosides in which a cyclic sugar unit is attached to the fatty alcohol by a glycoside bond and oligomeric glycosides with a degree of oligomerization of preferably up to about 8 are suitable. The degree of oligomerization is a statistical mean value on which the homolog distribution typical of such technical products is based.

Other suitable emulsifiers are anionic surfactants such as, for example, soaps, alkyl benzenesulfonates, alkanesulfonates, olefin sulfonates, alkylether sulfonates, glycerol ether sulfonates, α-methyl ester sulfonates, sulfofatty acids, alkylsulfates, fatty alcohol ether sulfates, glycerol ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates, acyl aspartates, alkyl oligoglucoside sulfates, protein fatty acid condensates (particularly wheat-based vegetable products) and alkyl(ether) phosphates. If the anionic surfactants contain polyglycol ether chains, they may have a conventional homolog distribution although they preferably have a narrow-range homolog distribution. Alkyl ether sulfates containing 12 to 18 carbon atoms in the alkyl group and 2 to 5 ethylene oxide units and fatty acid monoglyceride esulfates derived from fatty acids containing 12 to 18 carbon atoms are preferably used.

Zwitterionic surfactants may also be used as emulsifiers. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocoamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —$SO_3H$— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine. Besides the ampholytic emulsifiers, quaternary emulsifiers may also be used, those of the esterquat type, preferably methylquatemized difatty acid triethanolamine ester salts, being particularly preferred.

Wax Dispersions and o/w Emulsions

The wax dispersions to be used in accordance with the invention preferaby contain
(a) 1 to 50 and more particularly 10 to 30% by weight of waxes and
(b) 1 to 90 and more particularly 5 to 50% by weight of emulsifiers,
with the proviso that the quantities add up to 100% by weight with water and optionally polyols. The final dispersions are normally used in quantities of 1 to 15% by weight and more particularly 5 to 10% by weight, based on the emulsions. The production of the dispersions may be carried out by methods known per se and is not critical. The procedure normally comprises introducing an aqueous solution of the emulsifier and heating it to beyond the melting point of the wax, adding the molten wax and allowing the mixture to cool with intensive shearing. To produce the required o/w emulsions, the wax dispersions may then be stirred in cold, i.e. at temperatures of around 18 to 25° C.

Commercial Applications

The viscous o/w emulsions obtainable by the cold route in accordance with the invention are distinguished by high stability, even when stored at elevated temperature. They may contain mild surfactants, oils, superfatting agents, stabilizers, thickeners, polymers, silicone compounds, biogenic agents, deodorizers, anti-dandruff agents, filmformers, preservatives, hydrotropes, solubilizers, antioxidants, insect repellents, self-tanning agents, perfume oils, dyes and the like as further auxiliaries and additives. In one preferred embodiment of the invention, the o/w emulsions are sun protection emulsions which naturally contain UV protection factors.

Typical examples of suitable mild, i.e. dermatologically compatible, surfactants, are fatty alcohol polyglycol ether sulfates, monoglyceride sulfates, mono- and/or dialkylsulfosuccinates, fatty acid isethionates, fatty acid sarcosinates, fatty acid taurides, fatty acid glutamates, ether carboxylic acids, alkyl oligoglucosides, fatty acid glucamides, alkyl amidobetaines and/or protein fatty acid condensates (preferably based on wheat proteins).

Suitable oils are, for example, Guerbet alcohols based on fatty alcohols containing 6 to 18 and preferably 8 to 10 carbon atoms, esters of linear $C_{6-22}$ fatty acids with linear $C_{6-22}$ fatty alcohols, esters of branched $C_{6-13}$ carboxylic acids with linear $C_{6-22}$ fatty alcohols, esters of linear $C_{6-22}$ fatty acids with branched alcohols, more particularly 2-ethyl hexanol, esters of hydroxycarboxylic acids with linear or branched $C_{6-22}$ fatty alcohols, more particularly Dioctyl Malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-/di-/triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates, Guerbet carbonates, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group, ring opening products of epoxidized fatty acid esters with polyols, silicone oils and/or aliphatic or naphthenic hydrocarbons.

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Suitable thickeners are, for example, polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quatemized collagen polypeptides such as, for example, Lauryldimonium Hydroxypropyl Hydrolyzed Collagen (Lamequat® , Grünau GmbH), quaternized wheat polypeptides, polyethyleneimine, cationic silicone polymers such as, for example, Amidomethicone, copolymers of adipic acid and dimethylamino-hydroxypropyl diethylenetriamine (Cartaretine®, Sandoz AG), copolymers of acrylic acid with dimethyl diallyl ammonium chloride (Merquat® 550, Chemviron), polyaminopolyamides as described, for example, in FR-A 2 252 840 and crosslinked water-soluble polymers thereof, cationic chitin derivatives such as, for example, quaternized chitosan, optionally in microcrystalline distribution, condensation products of dihaloalkyls, for example dibromobutane, with bisdialkylamines, for example bis-dimethylamino-1,3-propane, cationic guar gum such as, for example, Jaguar®CBS, Jaguar®C-17, Jaguar®C-16 of Celanese, USA, quaterized ammonium salt polymers such as, for example, Mirapol® A-15, Mirapol® AD-1, Mirapol® AZ-1 of Miranol, USA.

Suitable anionic, zwitterionic, amphoteric and nonionic polymers are, for example, vinyl acetate/crotonic acid copolymers, vinyl pyrrolidonelvinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/ acrylate copolymers, octylacrylamide/methyl methacrylate/ tert.-butylaminoethyl methacrylate/2-hydroxypropyl methacrylate copolymers, polyvinyl pyrrolidone, vinyl pyrrolidone/vinyl acetate copolymers, vinyl pyrrolidone/ dimethylaminoethyl methacrylate/vinyl caprolactam terpolymers and optionally derivatized cellulose ethers and silicones.

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. In addition, a detailed review of suitable liquid silicones was published by Todd et al. in Cosm. Toil. 91, 27 (1976).

Typical examples of fats are glycerides while suitable waxes are inter alia beeswax, carnauba wax, candelilla wax, montan wax, paraffin wax or microwaxes, optionally in combination with hydrophilic waxes, for example cetyl stearyl alcohol or partial glycerides. Metal salts of fatty acids such as, for example, magnesium, aluminium and/or zinc stearate or ricinoleate may be used as stabilizers.

In the context of the invention, biogenic agents are, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts, and vitamin complexes.

Suitable deodorizers are, for example, antiperspirants, such as aluminium chlorohydrates. These antiperspirants are colorless hygroscopic crystals which readily deliquesce in air and which accumulate when aqueous aluminium chloride solutions are concentrated by evaporation. Aluminium chlorohydrate is used for the production of perspiration-inhibiting and deodorizing formulations and probably acts by partially blocking the sweat glands through the precipitation of proteins and/or polysaccharides [cf. J. Soc. Cosm. Chem. 24, 281 (1973)]. For example, an aluminium chlorohydrate which corresponds to the formula [Al$_2$(OH)$_5$Cl] .2.5H$_2$O and which is particularly preferred for the purposes of the invention is commercially available under the name of Locron® from Hoechst AG of Frankfurt, FRG [cf. J. Pharm. Pharmcol. 26, 531 (1975)]. Besides the chlorohydrates, aluminium hydroxylactates and acidic aluminium/zirconium salts may also be used. Other suitable deodorizers are esterase inhibitors, preferably trialkyl citrates, such as trimethyl citrate, tripropyl citrate, triisopropyl citrate, tributyl citrate and, in particular, triethyl citrate (Hydagen® CAT, Henkel KGaA, Düsseldorf, FRG). Esterase inhibitors inhibit enzyme activity and thus reduce odor formation. The free acid is probably released through the cleavage of the citric acid ester, reducing the pH value of the skin to such an extent that the enzymes are inhibited. Other esterase inhibitors are dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester. Antibacterial agents which influence the germ flora and destroy or inhibit the growth of perspiration-decomposing bacteria, may also be present in stick products.

Examples of such antibacterial agents are chitosan, phenoxyethanol and chlorhexidine gluconate. 5-Chloro-2-(2,4-dichlorophenoxy)-phenol, which is marketed under the name of Irgasan® by Ciba-Geigy of Basel, Switzerland, has also proved to be particularly effective.

Suitable antidandruff agents are climbazol, octopirox and zinc pyrithione. Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds. Suitable swelling agents for aqueous phases are montmorillonites, clays minerals, Pemulen and alkyl-modified Carbopol types (Goodrich). Other suitable polymers and swelling agents can be found in R. Lochhead's review in Cosm. Toil. 108, 95 (1993).

UV protection factors in the context of the invention are, for example, organic substances UV filters which are liquid or crystalline at room temperature and which are capable of absorbing ultraviolet radiation and of releasing the energy absorbed in the form of longer-wave radiation, for example heat. UV-B filters can be oil-soluble or water-soluble. The following are examples of oil-soluble substances:

3-benzylidene camphor or 3-benzylidene norcamphor and derivatives thereof, for example 3-(4-methylbenzylidene)-camphor as described in EP-B1 0693471;

4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;

esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);

esters of salicylic acid, preferably salicylic acid-2-ethylhexyl ester, salicylic acid-4-isopropylbenzyl ester, salicylic acid homomenthyl ester;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably 4-methoxybenzalmalonic acid di-2-ethylhexyl ester;

triazine derivatives such as, for example, 2,4,6-trianilino-(p-carbo-2'-ethyl-1'-hexyloxy)-1,3,5-triazine and Octyl Triazone as described in EP-A1 0818450;

propane-1,3-diones such as, for example, 1-(4-tert.butylphenyl)-3-(4'-methoxyphenyl)-propane-1,3-dione;

ketotricyclo(5.2.1.0)decane derivatives as described in EP-B1 0694521.

Suitable water-soluble substances are 2-phenylbenzimidazole-5-sulfonic acid and alkali metal, alkaline earth metal, ammonium, alkylammonium, alkanolammonium and glucammonium salts thereof;

sulfonic acid derivatives of benzophenones, preferably 2-hydroxy-4-methoxybenzophenone-5-sulfonic acid and salts thereof;

sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example 1-(4'-tert.butylphenyl)-3-(4'-methoxyphenyl)-propane-1,3-dione, 4-tert.butyl-4'-methoxydibenzoyl methane (Parsol 1789) or 1-phenyl-3-(4'-isopropylphenyl)-propane-1,3-dione. The UV-A and UV-B filters may of course also be used in the form of mixtures. Besides the soluble substances mentioned, insoluble light-blocking pigments, i.e. finely dispersed metal oxides or salts, for example titanium dioxide, zinc oxide, iron oxide, aluminium oxide, cerium oxide, zirconium oxide, silicates (talcum), barium sulfate and zinc stearate, may also be used for this purpose. The particles should have a mean diameter of less than 100 nm, preferably between 5 and 50 nm and more preferably between 15 and 30 nm. They may be spherical in shape although ellipsoidal particles or other non-spherical particles may also be used. Other suitable UV filters can be found in P. Finkel's review in S ÖFW-Journal 122, 543 (1996).

Besides the two groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmole to μmole/kg) also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitarnin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, Superoxid-Dismutase, zinc and derivatives thereof (for example ZnO, ZnSO$_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

In addition, hydrotropes, for example ethanol, isopropyl alcohol or polyols, may be used to improve flow behavior.

Suitable polyols preferably contain 2 to 15 carbon atoms and at least two hydroxyl groups. Typical examples are glycerol;

alkylene glycols such as, for example, ethylene glycol, diethylene glycol, propylene glycol, butylene glycol, hexylene glycol and polyethylene glycols with an average molecular weight of 100 to 1000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

aminosugars, for example glucamine.

Suitable preservatives are, for example, phenoxyethanol, formaldehyde-solution, parabens, pentanediol or sorbic acid and the other classes of compounds listed in Appendix 6, Parts A and B of the Kosmetikverordnung ("Cosmetics Directive"). Suitable insect repellents are N,N-diethyl-m-toluamide, pentane-1,2-diol or Insect Repellent 3535. A suitable self-tanning agent is dihydroxyacetone.

Suitable perfume oils are mixtures of natural and synthetic fragrances. Natural fragrances include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamon, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, labolanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillate, irotyl and floramate.

Suitable dyes are any of the substances suitable and approved for cosmetic purposes as listed, for example, in the publication "Kosmetische Färbemittel" of the Farbstoffkommission der Deutschen Forschungs-gemeinschaft, Verlag Chemie, Weinheim, 1984, pages 81 to 106. These dyes are normally used in concentrations of 0.001 to 0.1% by weight, based on the mixture as a whole.

The total percentage content of auxiliaries and additives may be from 1 to 50% by weight and is preferably from 5 to 40% by weight, based on the particular formulation.

EXAMPLES

Two wax dispersions with the compositions shown in Table 1 were produced by the PIT process. Four o/w emulsions were then prepared by mixing the ingredients at 20° C. Their viscosities were determined by the Brookfield method using an RVF viscosimeter (23° C., spindle 5, 10 r.p.m.). The results are set out in Table 2. Examples 1 to 4 correspond to the invention while Examples C1 and C2 are intended for comparison.

TABLE 1

Wax dispersions

| Composition | WD1 | WD2 |
|---|---|---|
| Ethyleneglycol Stearate | 20.0 | — |
| Glyceryl Stearate | 5.0 | 20.0 |
| Cocoglucoside | 15.0 | 5.0 |
| Cocamidopropyl Betaine | — | 10.0 |
| Water | to 100 | |

TABLE 2

| Composition/performance | Viscosity of o/w emulsions | | | | | |
|---|---|---|---|---|---|---|
| | 1 | 2 | 3 | 4 | C1 | C2 |
| Wax dispersion 1 | 6.5 | 6.5 | — | — | — | — |
| Wax dispersion 2 | — | — | 6.5 | 6.5 | — | — |
| Ethyleneglycol Stearate | — | — | — | — | 6.5 | — |
| Glyceryl Stearate | 0.5 | 0.5 | 0.5 | 0.5 | 0.5 | 7.0 |
| Polyglyceryl-2 Dihydroxystearate | — | 0.7 | — | 0.7 | — | — |
| Coconut oil | 10.0 | 10.0 | 10.0 | 10.0 | 10.0 | 10.0 |
| Castor oil | 2.0 | 2.0 | 2.0 | 2.0 | 2.0 | 2.0 |
| Vaseline | 2.0 | 2.0 | 2.0 | 2.0 | 2.0 | 2.0 |
| Carbomer (2% swelling) | 25.0 | 25.0 | — | — | 25.0 | 25.0 |
| Xanthan Gum/Magnesium Aluminium Silicate 1:1 | — | — | 2.0 | 2.0 | — | — |
| Glycerin (86% by weight) | 2.0 | 2.0 | 2.0 | 2.0 | 2.0 | 2.0 |
| Water | to 100 | | | | | |
| Viscosity [mPas] | | | | | | |
| Immediate | 16400 | 16800 | 9600 | 9600 | 12100 | 11800 |
| after 2 w/40° C. | 16100 | 16300 | 9200 | 9200 | — | — |
| Stability | Stable | Stable | Stable | Stable | Unstable | Unstable |
| Sensorial evaluation | | Substantial | | | Insubstantial | |

What is claimed is:

1. A process for cold-producing an oil-in-water emulsion having enhanced consistency and tactile properties comprising:
   (a) providing an oil component;
   (b) providing an aqueous wax dispersion containing:
      (i) a wax component; and
      (ii) an emulsifier;
   (c) providing water; and,
   (d) cold-stirring (a)–(c) to form the emulsion.

2. The process of claim 1 wherein the wax component is present in the wax dispersion in an amount of from 1 to 50% by weight, based on the weight of the aqueous wax dispersion.

3. The process of claim 1 wherein the wax component is present in the aqueous wax dispersion in an amount of from 10 to 30% by weight, based on the weight of the aqueous wax dispersion.

4. The process of claim 1 wherein the emulsifier is present in the aqueous wax dispersion in an amount of from 1 to 90% by weight, based on the weight of the aqueous wax dispersion.

5. The process of claim 1 wherein the emulsifier is present in the aqueous wax dispersion in an amount of from 5 to 50% by weight, based on the weight of the aqueous wax dispersion.

6. The process of claim 1 wherein the aqueous wax dispersion is employed in an amount of from 1 to 15% by weight, based on the weight of the emulsion.

7. The process of claim 1 wherein the aqueous wax dispersion is employed in an amount of from 5 to 10% by weight, based on the weight of the emulsion.

8. The process of claim 1 wherein (a)–(c) is cold-stirred at a temperature of from 18 to 25° C.

* * * * *